US012394080B2

(12) United States Patent
Rajguru et al.

(10) Patent No.: US 12,394,080 B2
(45) Date of Patent: Aug. 19, 2025

(54) INTRALUMINAL IMAGE-BASED VESSEL DIAMETER DETERMINATION AND ASSOCIATED DEVICES, SYSTEMS, AND METHODS

(71) Applicant: PHILIPS IMAGE GUIDED THERAPY CORPORATION, San Diego, CA (US)

(72) Inventors: Nikhil Sreedhar Rajguru, San Diego, CA (US); Bernhard Sturm, Davis, CA (US); David Chalyan, Oceanside, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 420 days.

(21) Appl. No.: 17/782,733

(22) PCT Filed: Dec. 4, 2020

(86) PCT No.: PCT/EP2020/084656
§ 371 (c)(1),
(2) Date: Jun. 6, 2022

(87) PCT Pub. No.: WO2021/115958
PCT Pub. Date: Jun. 17, 2021

(65) Prior Publication Data
US 2023/0008714 A1   Jan. 12, 2023

Related U.S. Application Data

(60) Provisional application No. 62/946,097, filed on Dec. 10, 2019.

(51) Int. Cl.
*G06T 7/62* (2017.01)
*A61B 5/107* (2006.01)
*A61B 34/10* (2016.01)

(52) U.S. Cl.
CPC ............. *G06T 7/62* (2017.01); *A61B 5/1076* (2013.01); *A61B 34/10* (2016.02);
(Continued)

(58) Field of Classification Search
CPC ............. G06T 7/62; G06T 2207/10101; G06T 2207/10132; G06T 2207/30101; A61B 34/10; A61B 5/1076; A61B 2034/108
See application file for complete search history.

(56) References Cited

U.S. PATENT DOCUMENTS 6,200,268 B1   3/2001   Vince
6,381,350 B1   4/2002   Klingensmith
(Continued)

FOREIGN PATENT DOCUMENTS

JP   2001079097 A   *   3/2001
WO   2014092755 A1   6/2014

OTHER PUBLICATIONS

International Search Report and Written Opinion of PCT/EP2020/084656, dated Feb. 22, 2021.

*Primary Examiner* — Syed Haider

(57) ABSTRACT

Disclosed is an intraluminal imaging system, including an intraluminal imaging catheter or guidewire configured to be positioned within an anatomy of a patient, and a processor circuit in communication with the imaging catheter or guidewire, wherein the processor circuit is configured to receive a plurality of cross-sectional images of the anatomy from the imaging catheter or guidewire. The processor is further configured to compute, using image processing of at least one of the cross-sectional images, a value of the anatomy, estimate a cross-sectional shape of the anatomy to be circular, calculate a diameter of the anatomy based on the computed value and the estimated circular shape, and output the diameter of the anatomy to a display.

18 Claims, 10 Drawing Sheets

(52) U.S. Cl.
CPC .................. *A61B 2034/108* (2016.02); *G06T 2207/10101* (2013.01); *G06T 2207/10132* (2013.01); *G06T 2207/30101* (2013.01)

(56) References Cited

U.S. PATENT DOCUMENTS

| | | | |
|---|---|---|---|
| 7,074,188 B2 | 7/2006 | Nair | |
| 7,175,597 B2 | 2/2007 | Vince | |
| 7,215,802 B2 | 5/2007 | Klingensmith | |
| 7,359,554 B2 | 4/2008 | Klingensmith | |
| 7,463,759 B2 | 12/2008 | Klingensmith | |
| 7,846,101 B2 | 12/2010 | Eberle | |
| 2011/0071404 A1* | 3/2011 | Schmitt | A61B 5/0066 382/128 |
| 2011/0295107 A1* | 12/2011 | Kargar | A61B 5/1076 600/481 |
| 2015/0297373 A1* | 10/2015 | Schmitt | A61F 2/86 623/1.16 |
| 2017/0236275 A1* | 8/2017 | Jung | A61B 8/5223 382/131 |
| 2017/0281375 A1* | 10/2017 | Longo | A61F 2/89 |
| 2018/0271614 A1* | 9/2018 | Kunio | A61B 90/37 |
| 2019/0282182 A1 | 9/2019 | Scott | |
| 2019/0282199 A1 | 9/2019 | Merritt | |
| 2020/0029861 A1 | 1/2020 | Rajguru | |
| 2020/0029932 A1 | 1/2020 | Cohen | |
| 2020/0129142 A1 | 4/2020 | Chao | |
| 2020/0129143 A1 | 4/2020 | Di Tullio | |
| 2020/0129147 A1 | 4/2020 | Nair | |
| 2020/0129148 A1 | 4/2020 | Jenkins | |
| 2020/0129158 A1 | 4/2020 | Chao | |
| 2020/0129159 A1 | 4/2020 | Rajguru | |

\* cited by examiner

INTRALUMINAL IMAGE-BASED VESSEL DIAMETER DETERMINATION AND ASSOCIATED DEVICES, SYSTEMS, AND METHODS

TECHNICAL FIELD

The subject matter described herein relates to a system for intraluminal medical imaging. In particular, the disclosed system provides a system for computing geometrically derived vessel measurements in real time or near real time based on intravascular ultrasound (IVUS) or other intraluminal images obtained during a pullback procedure.

BACKGROUND

Various types of intraluminal (also referred to as intravascular) imaging systems are used in diagnosing and treating diseases. For example, intravascular ultrasound (IVUS) imaging is widely used in interventional cardiology as a diagnostic tool for visualizing vessels within a body of a patient. This may aid in assessing diseased vessels, such as an arteries and veins within the human body, to determine the need for treatment, to optimize treatment, and/or to assess the effectiveness of treatments such as angioplasty and stenting, IVC-filter retrieval, and EVAR and FEVAR (and similar on the abdominal trait) atherectomy. Different diseases, implants, and medical procedures produce physical features with different sizes, structures, densities, water contents, and accessibilities for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object that may be placed in a vessel or lumen to hold the vessel or lumen open to a particular diameter. A compression occurs when anatomical structures outside the vessel or lumen impinge on the vessel or lumen, constricting it. A thrombus occurs when a blood clot forms within the lumen of a vessel. Compression and thrombus are both examples of stenosis, e.g., a narrowing of the vessel. A stenosis may also occur when other material (e.g., plaque) accumulates within the lumen of a vessel.

In some cases, intraluminal medical imaging is carried out with an intraluminal imaging device, such as an IVUS catheter including one or more ultrasound transducers. The IVUS catheter is passed into the vessel and guided to the area to be imaged. The transducers emit ultrasonic energy and receive ultrasound echoes reflected from the vessel. The ultrasound echoes are processed to create a cross-sectional image of the vessel at one or more regions of interest. The image of the vessel may include one or more lesions or blockages in the vessel, implants, and other geometric features. For example, a stent may be placed within the vessel to treat or correct blockages, and intraluminal imaging may be carried out to view the placement of the stent within the vessel. Other types of treatment include thrombectomy, ablation, angioplasty, pharmaceuticals, etc.

In vascular procedures, vessel measurements are used to facilitate clinical decision making such as stent sizing. Stent sizes are defined by the stent diameter and stent length. Vessel measurements can be obtained from intraluminal image data (IVUS or OCT). In some aspects, obtaining accurate vessel measurements may be challenging or problematic because stenoses (e.g., compression, thrombus) can cause complex cross-sectional vessel shapes, including concave vessel geometries in the region of the stenosis, leading to inaccurate vessel size measurements and thus inaccurate stent sizing.

The information included in this Background section of the specification, including any references cited herein and any description or discussion thereof, is included for technical reference purposes only and is not to be regarded as subject matter by which the scope of the disclosure is to be bound.

SUMMARY

Disclosed are systems, methods, and associated devices for advantageously computing geometrically derived vessel measurements in real time or near real time based on intraluminal ultrasound images, or other image types, obtained during a pullback procedure. In particular, the current disclosure provides a system and method for deriving vessel diameter measurements (hereinafter referred to as "intrinsic diameter" measurements) based on identification and quantification of geometric features of the vessel, such as lumen boundary, cross-sectional area, and/or volume. The method applies to all vessel geometries but may be particularly relevant to, and represents a substantial improvement for, concave (e.g., bean-shaped) lumen cross sections where direct diameter measurements can be challenging. The system may be referred to as a lumen intrinsic diameter measurement system.

The lumen intrinsic diameter measurement system disclosed herein has particular, but not exclusive, utility for intraluminal ultrasound imaging procedures. In one embodiment, the lumen intrinsic diameter measurement system includes an intraluminal imaging system including: an intraluminal imaging catheter or guidewire configured to be positioned within an anatomy of a patient; a processor circuit in communication with the intraluminal imaging catheter or guidewire, where the processor circuit is configured to: receive a plurality of cross-sectional images of the anatomy from the intraluminal imaging catheter or guidewire; compute, using image processing of a cross-sectional image of the plurality of cross-sectional images, a value of the anatomy; estimate a cross-sectional shape of the anatomy to be circular; calculate a diameter of the anatomy based on the computed value and the estimated circular cross-sectional shape; and output the diameter of the anatomy to a display in communication with the processor circuit. Other examples of this embodiment include corresponding computer systems, apparatus, and computer programs recorded on one or more computer storage devices, each configured to perform the actions of the methods.

Implementations may include one or more of the following features. The intraluminal imaging system where the value includes a perimeter of the anatomy. The intraluminal imaging system where the value includes a cross-sectional area of the anatomy. The intraluminal imaging system where the value includes a volume of the anatomy. The intraluminal imaging system where the value includes at least two of a perimeter, a cross-sectional area, or a volume of the anatomy. The intraluminal imaging system where the processor circuit is further configured to compute a stent diameter that is equal to the calculated diameter of the anatomy multiplied by a scaling factor. The intraluminal imaging system further including a user interface in communication with the processor circuit, where the user interface is configured to accept inputs from a user, and where the processor circuit is further configured to, in response to receiving inputs from the user interface: calculate the stent diameter; and output the stent diameter to the display; calculate a stent length based on the plurality of cross-sectional images; and output the stent length to the display. The intraluminal imaging system where the anatomy is a blood vessel. Implementations of the described techniques may include hardware, a method or process, or computer software on a computer-accessible medium.

One embodiment includes a method for computing lumen diameters for intraluminal medical procedures, the method including: receiving, by a processor circuit, a plurality of cross-sectional images of an anatomy of a patient, where the plurality of cross-sectional images is obtained by an intraluminal imaging catheter or guidewire positioned within the anatomy; computing, using image processing by the processor circuit of a cross-sectional image of the plurality of cross-sectional images, a value of the anatomy; estimating a cross-sectional shape of the anatomy to be circular; calculating a diameter of the anatomy based on the computed value and the estimated circular cross-sectional shape of the anatomy; and outputting the diameter of the anatomy to a display in communication with the processor circuit. Other examples of this embodiment include corresponding computer systems, apparatus, and computer programs recorded on one or more computer storage devices, each configured to perform the actions of the methods.

Implementations may include one or more of the following features. The method where the value includes a perimeter of the anatomy. The method where the value includes cross-sectional area of the anatomy. The method where the value includes a volume of the anatomy. The method where the value includes at least two of a perimeter, a cross-sectional area, or a volume of the anatomy. The method further including computing a stent diameter that is equal to the calculated diameter of the anatomy multiplied by a scaling factor. The method further including, in response to inputs received from a user interface: calculating the stent diameter; and outputting the stent diameter to the display; calculating a stent length based on the plurality of cross-sectional images; and outputting the stent length to the display. The method where the anatomy is a blood vessel. Implementations of the described techniques may include hardware, a method or process, or computer software on a computer-accessible medium.

One embodiment includes a system for intravascular imaging, the system including: an intravascular imaging catheter or guidewire; and a processor circuit in communication with the intravascular imaging catheter or guidewire, where the processor circuit is configured to: receive a plurality of cross-sectional images of a blood vessel captured by the intravascular imaging catheter or guidewire; calculate an intrinsic diameter associated with the blood vessel based on the plurality of cross-sectional images; calculate a stent diameter based on the intrinsic diameter; output the stent diameter to a display in communication with the processor circuit. Other examples of this embodiment include corresponding computer systems, apparatus, and computer programs recorded on one or more computer storage devices, each configured to perform the actions of the methods.

Implementations may include one or more of the following features. The system where the processor circuit is configured to calculate the intrinsic diameter associated with the blood vessel based on an estimation of a circular cross section for the blood vessel, and at least one of a lumen perimeter measurement, a lumen area measurement, or a lumen volume measurement. Implementations of the described techniques may include hardware, a method or process, or computer software on a computer-accessible medium.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the lumen intrinsic diameter measurement system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
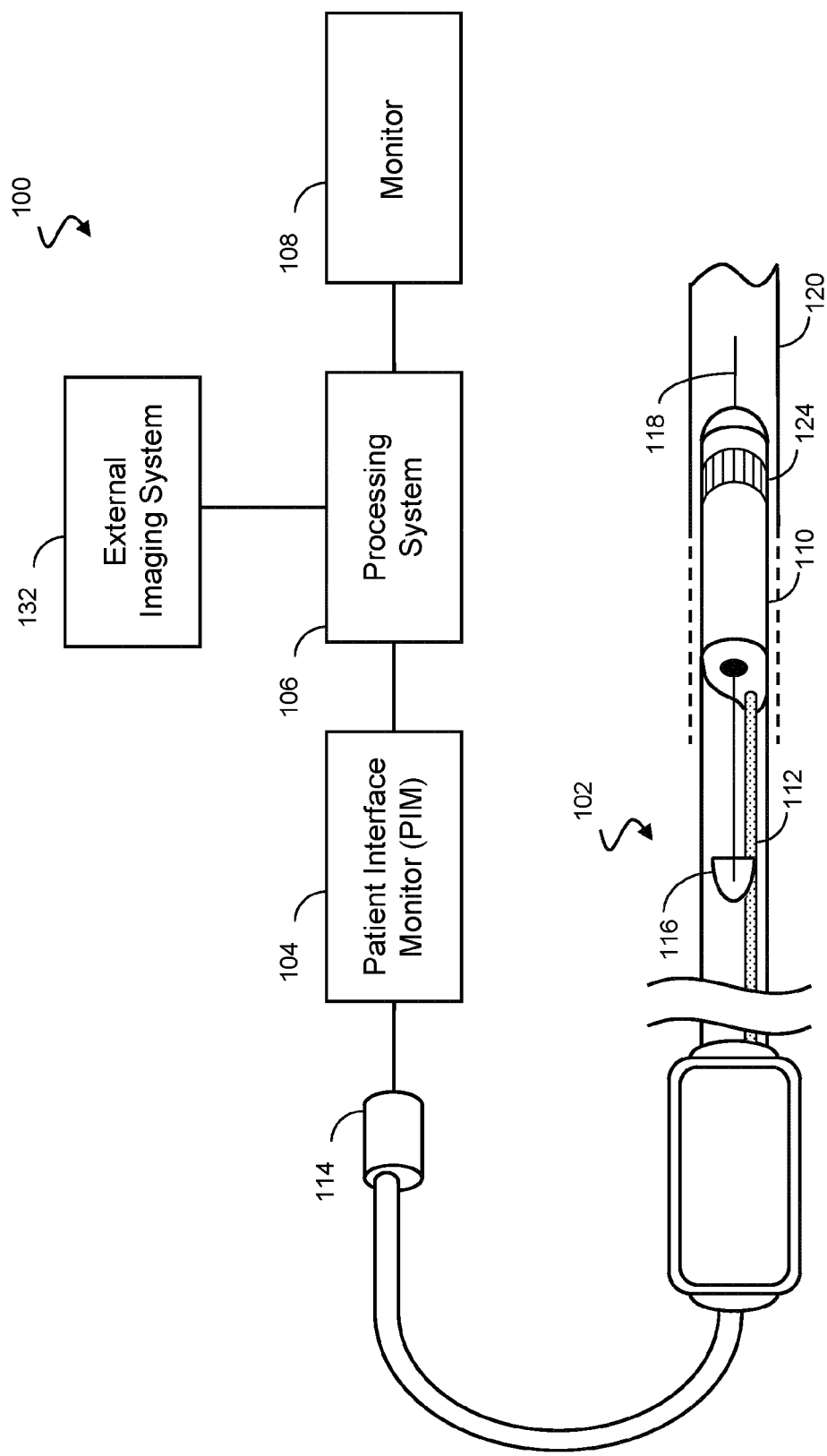
FIG. 1 is a diagrammatic schematic view of an intraluminal imaging system, according to aspects of the present disclosure.

The present disclosure relates generally to intraluminal medical imaging, including imaging associated with a body lumen of a patient using an intraluminal imaging device. In some instances, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages, and intraluminal imaging may be carried out to view the placement of the stent within the vessel. Other types of treatment include thrombectomy, ablation, angioplasty, pharmaceuticals, etc.

As described above, intraluminal imaging may be used to obtain vessel measurements in order to select a stent having a size (e.g., diameter, circumference) appropriate for the stented section of the vessel. One approach to obtaining vessel measurements may include measuring a distance between all the point combinations from vascular contours that pass through the lumen center, identifying the minimum and maximum diameters of the lumen, and estimating an average diameter as the average of the min and max diameters. However, this approach may assume a convex contour (e.g., a vessel of essentially elliptical cross section), and may fail to account for complex and/or concave vessel geometries (e.g., vessels with bean-shaped cross sections).

The present disclosure provides systems, methods, and devices for advantageously computing geometrically derived vessel measurements in real time or near real time based on intravascular images (e.g., IVUS, optical coherence tomography (OCT), photographic, etc.) obtained during a pullback procedure. In particular, the current disclosure provides a system, apparatus, and method for deriving vessel diameter measurements based on the identification and quantification of the geometric features of the vessel, including lumen boundaries, cross-sectional area, and volume. In that regard, an intrinsic vessel diameter can be derived from a vascular contour, perimeter, area, and/or volume measurement by using the mathematical formulas described herein and an assumption of a circular vascular geometry, referred to hereinafter as an "intrinsic diameter." The intrinsic diameter may in some cases be used to select a stent diameter.

The present disclosure provides algorithms, relationships, and mathematical formulas to derive a vessel diameter measurement that can subsequently be used for vessel and stent sizing purposes, along with an apparatus and systems for capturing the required precursor measurements and reporting the results to a user. In some aspects, the geometrically derived diameter ("intrinsic diameter") calculations allow for reliable vessel diameter measurement and/or stent sizing for vessels having a variety of shapes, contours, or cross-sections, without necessarily checking all contour point combinations to identify minimum and maximum diameters. Embodiments of the present disclosure may be particularly relevant for vessels with concave cross sections which can make direct measurements from the vascular contours harder to obtain. According to the embodiments of the present disclosure, the algorithms are predicated on the tendency of vessels to assume a circular cross section rather than any other shape, especially though not exclusively in cases where a circular stent is expanded within them. Assuming a circular vessel geometry to extract diameter measurements from contour, perimeter, area, or volume measurements, is thus a practical means of making vessel measurements that lead to more accurate stent sizing that may be associated with improved clinical outcomes. The method may apply to all geometries but is particularly relevant to, and represents a substantial improvement for, concave (e.g., bean-shaped) lumen cross sections where direct diameter measurements can be challenging. In some aspects, the system may be hereinafter referred to as a lumen intrinsic diameter measurement system.

The lumen intrinsic diameter measurement system provides a quantitative output, the intrinsic diameter, which may be used to select a stent diameter that will, for example, optimally expand the vessel without stretching it.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. 62/642,847, filed Mar. 14, 2018 (and a Non-Provisional Application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional Application filed therefrom on Mar. 15, 2019 as U.S. Ser. No. 16/354,970), each of which is hereby incorporated by reference in its entirety as though fully set forth herein.

Embodiments of the present disclosure substantially aid a clinician in determining a stent diameter for optimal expansion of a vessel (e.g., maximum expansion without stretching), by providing a geometrically derived value for an idealized vessel diameter (e.g., the diameter of the vessel if it were circular). Implemented on a medical imaging console (e.g., an IVUS imaging console) in communication with a medical imaging sensor (e.g., an intraluminal ultrasound sensor), the lumen intrinsic diameter measurement system disclosed herein provides both time savings and an improvement in the accuracy of stent sizing. The disclosed embodiments may provide a quantitative, repeatable process that involves fewer and simpler steps to be taken by the clinician or other user. This occurs for example without the normally routine need for identifying the narrowest point of a vessel, measuring minimum and maximum diameters of the vessel lumen at that narrowest point, and averaging the minimum and maximum diameter to yield an estimated diameter. This unconventional approach improves the functioning of the medical imaging console and sensor, by outputting a single quantitative value—the intrinsic diameter—that can in some cases be used directly as a stent diameter.

The lumen intrinsic diameter measurement system may be implemented as a set of computer program instructions, logical branches, and/or mathematical operations, whose outputs are viewable on a display, and operated by a control process executing on a processor that accepts user inputs (e.g., from a user interface such as a keyboard, mouse, or touchscreen interface), and that is in communication with one or more medical imaging sensors (e.g., intraluminal ultrasound sensors). In that regard, the control process performs certain operations in response to different inputs or selections made by a user at the start of an imaging procedure, and may also respond to inputs made by the user during the procedure.

These descriptions are provided for exemplary purposes only, and should not be considered to limit the scope of the lumen intrinsic diameter measurement system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. Further, while the embodiments below refer specifically to intravascular ultrasound (IVUS) imaging devices and procedures, the present disclosure also contemplates other types of imaging devices, systems, and procedures, including but not limited to OCT, TEE, angiography/venography, external ultrasound imaging, and combinations thereof. For the sake of brevity, however, the numerous iterations of these combinations will not be described separately.

FIG. 1 is a diagrammatic schematic view of an intraluminal imaging system incorporating the lumen intrinsic diameter measurement system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), optical coherence tomography (OCT), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging (e.g., OCT), photographic, etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed for example in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System (HIS) via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 100000 acoustic elements, including values such as 2 acoustic elements, 4 acoustic elements, 36 acoustic elements, 64 acoustic elements, 128 acoustic elements, 500 acoustic elements, 812 acoustic elements, 1,000 acoustic elements, 5,000 acoustic elements, 10,000 acoustic elements, 65,000 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Koninklijke Phlips N. V. and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of a variety of different the displays or visualizations (e.g., display 400 of FIG. 4, below).

The external imaging system 132 can be configured to obtain x-ray, radiographic, angiographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
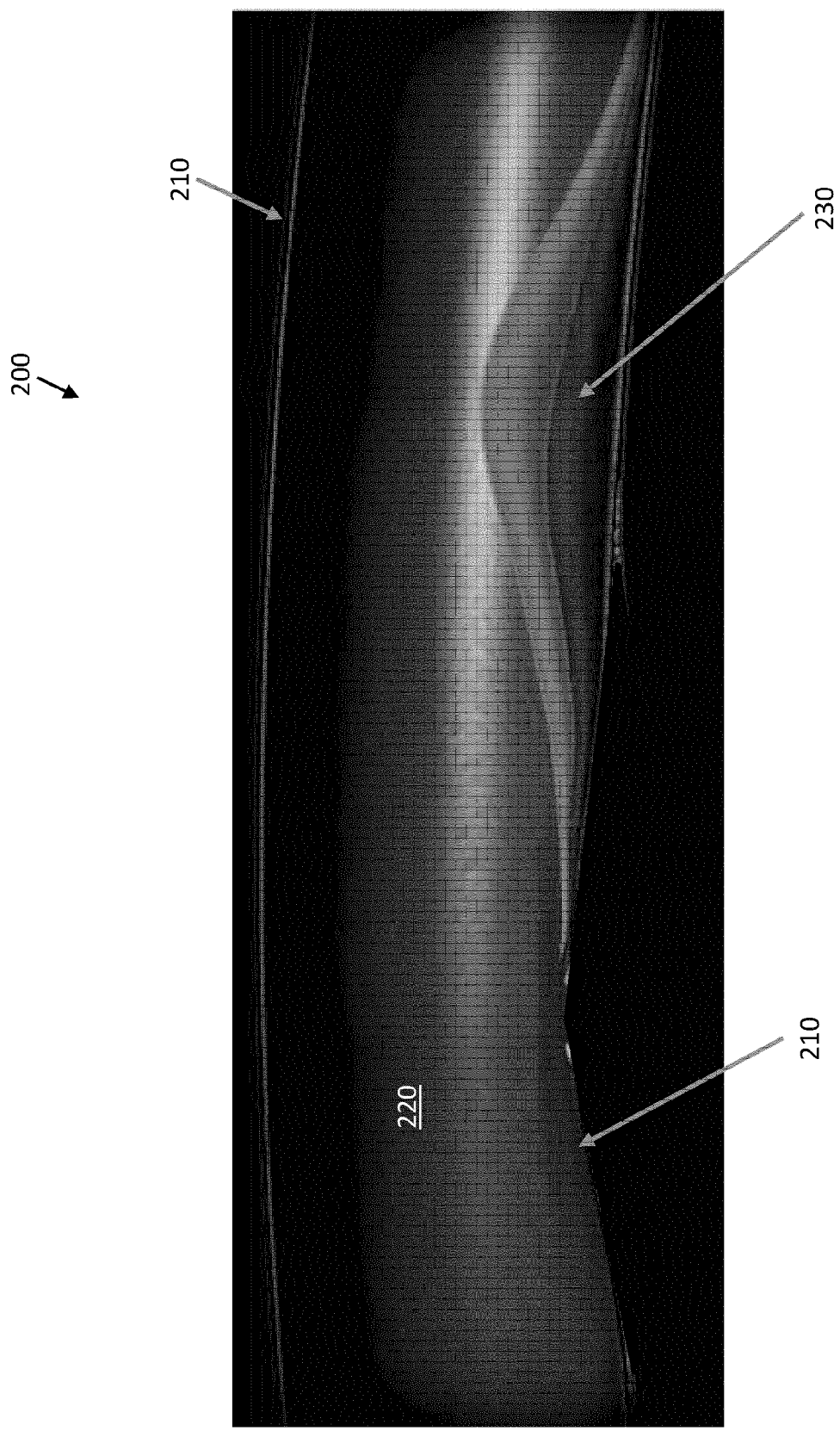
FIG. 2 is a longitudinal cross-sectional view of a blood vessel incorporating a stenosis, according to aspects of the present disclosure.

FIG. 2 illustrates a longitudinal cross sectional view of a blood vessel 200 that includes a stenosis 230. The stenosis 230 may occur inside the vessel walls 210 (e.g., a thrombus, clot, or plaque) or outside the vessel walls 210 (e.g., a compression), and may restrict the flow of blood through the lumen 220. Compression may be caused by other anatomical structures outside the blood vessel 200, including but not limited to a tendon, ligament, or neighboring lumen. As mentioned above, the presence of the stenosis 230 within the blood vessel 200 causes a non-circular luminal cross section or contour. For example, in some aspects, the stenosis 230 may create a partially concave region within the vessel 230 that may otherwise comprise convex, or mostly convex regions.

Figure 3:
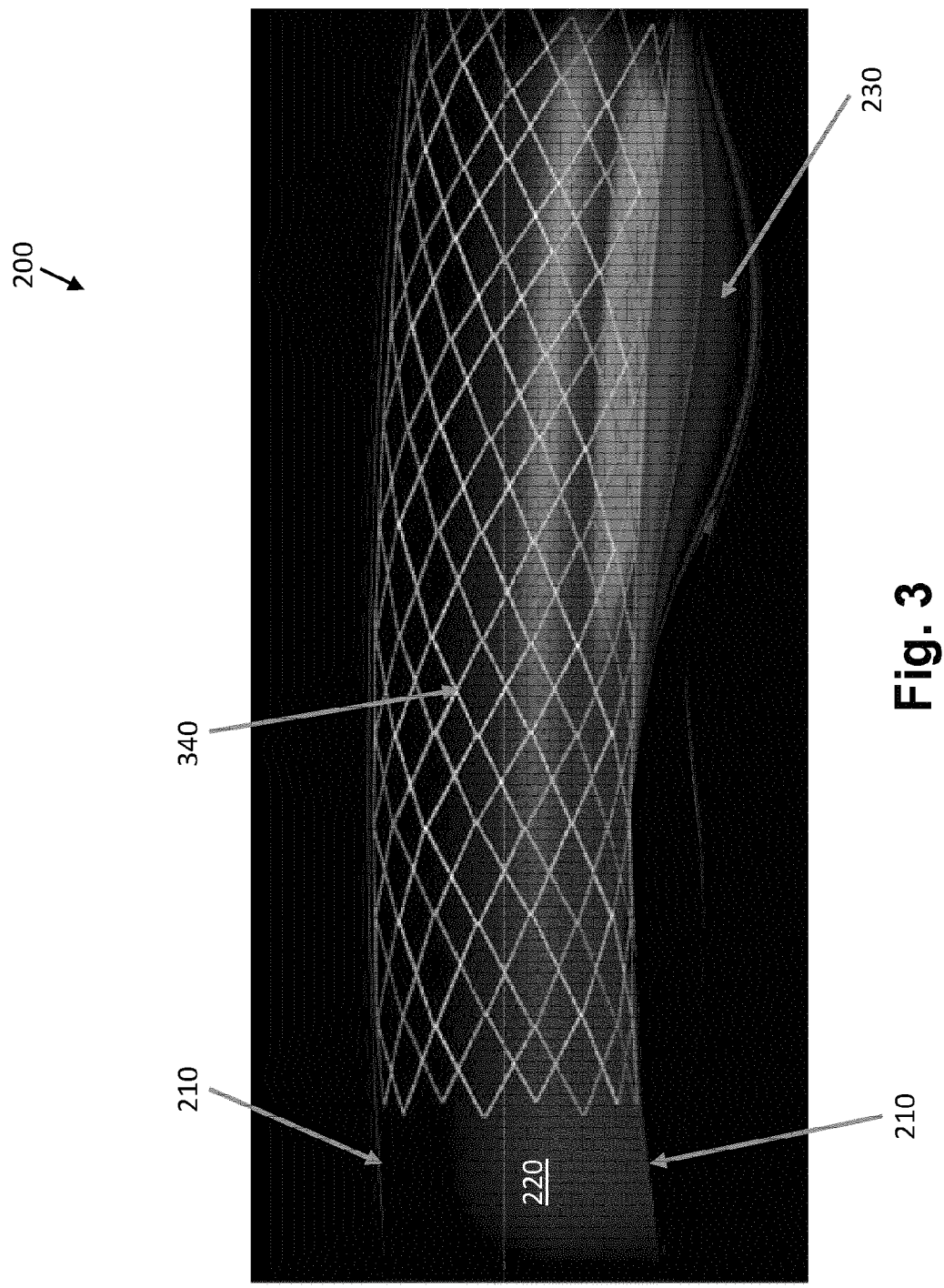
FIG. 3 is a longitudinal cross-sectional view of a blood vessel incorporating a stenosis and propped open with a stent 340, according to aspects of the present disclosure.

FIG. 3 illustrates a longitudinal cross sectional of a blood vessel 200 having a stenosis 230, and a stent 340 positioned within the blood vessel 200 to expand or open a narrowed region of the vessel caused by the stenosis 230. The stent 340 displaces and arrests the stenosis 230, pushing the vessel walls 210 outward, thus reducing the flow restriction for the blood through the lumen 220. In some aspects, the stent 340 has a size (e.g., diameter, circumference, cross-sectional area) that forces the vessel walls 210 to assume a circular, or substantially circular cross section in the area of the stenosis 230. The stent 340 may be selected such that its size corresponds to the size of the lumen 220 of the vessel 200 in the area of the stenosis 230, and assuming a circular cross section. Other treatment options for alleviating an occlusion may include but are not limited to thrombectomy, ablation, angioplasty, and pharmaceuticals. However, in many cases it may be desirable to obtain accurate and timely intravascular images of the affected area, along with accurate and detailed knowledge of the location, orientation, length, and volume of the affected area prior to, during, or after treatment.

Figure 4:
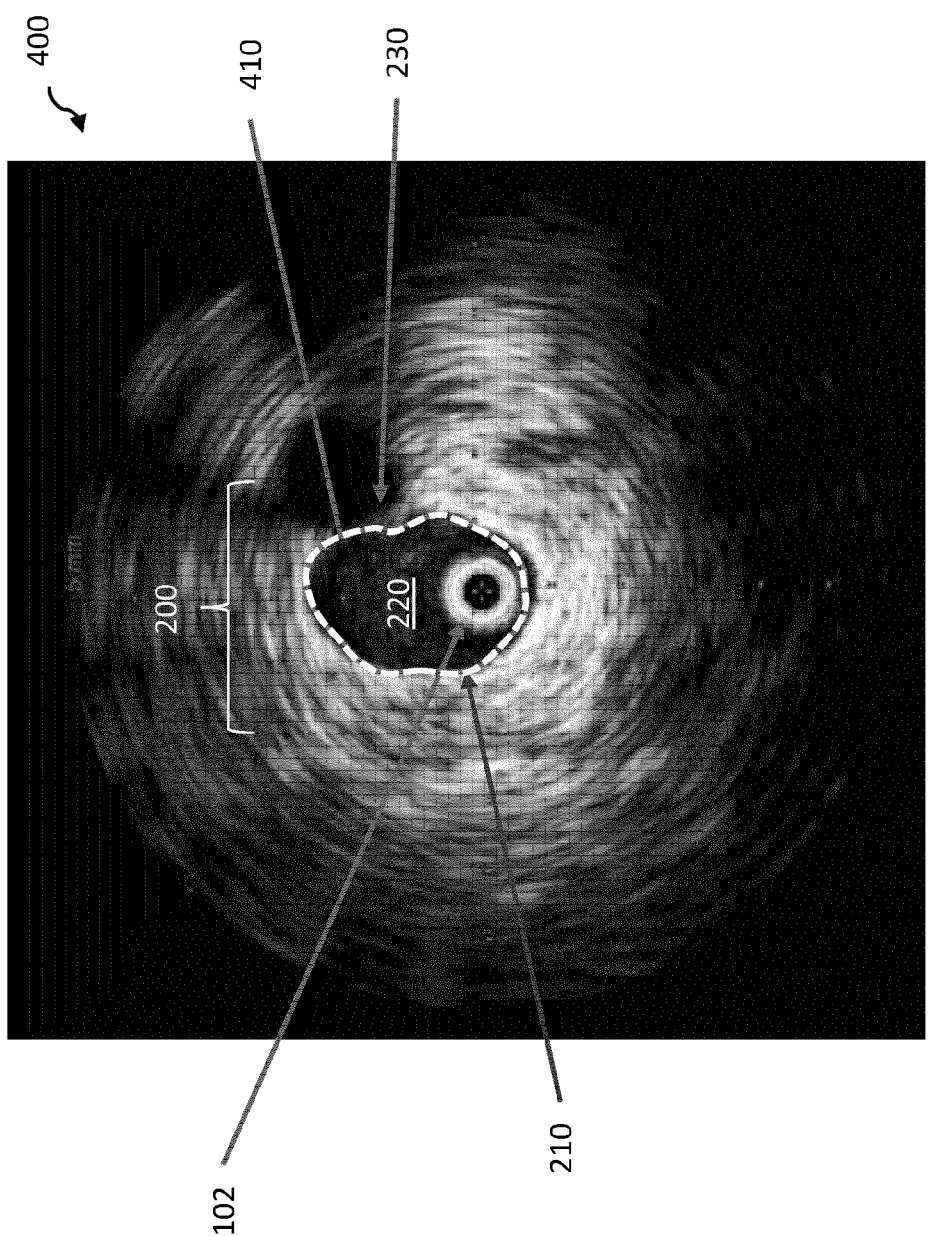
FIG. 4 is an IVUS image of a radial or axial cross section of a blood vessel captured during an intravascular imaging procedure, according to aspects of the present disclosure.

FIG. 4 is an IVUS image 400 of a radial or axial cross sectional view (i.e. a cross section perpendicular to the longitudinal axis) of a blood vessel 200 captured during an intravascular imaging procedure. The radial cross-sectional view is associated with an imaging plane that is perpendicular to a longitudinal axis of the blood vessel 200. Visible are the intraluminal imaging probe 102, vessel wall 210, lumen 220, and a compression 230. The perimeter 410 of the vessel wall 210 has been identified and marked. Depending on the implementation, this may be accomplished manually through a user interface (e.g., drawing on a touch screen), or automatically by an algorithm, as discussed below. The perimeter 410 comprises a non-circular cross-sectional profile, including a concave or partially concave portion in the area of the compression 230.

Figure 5:
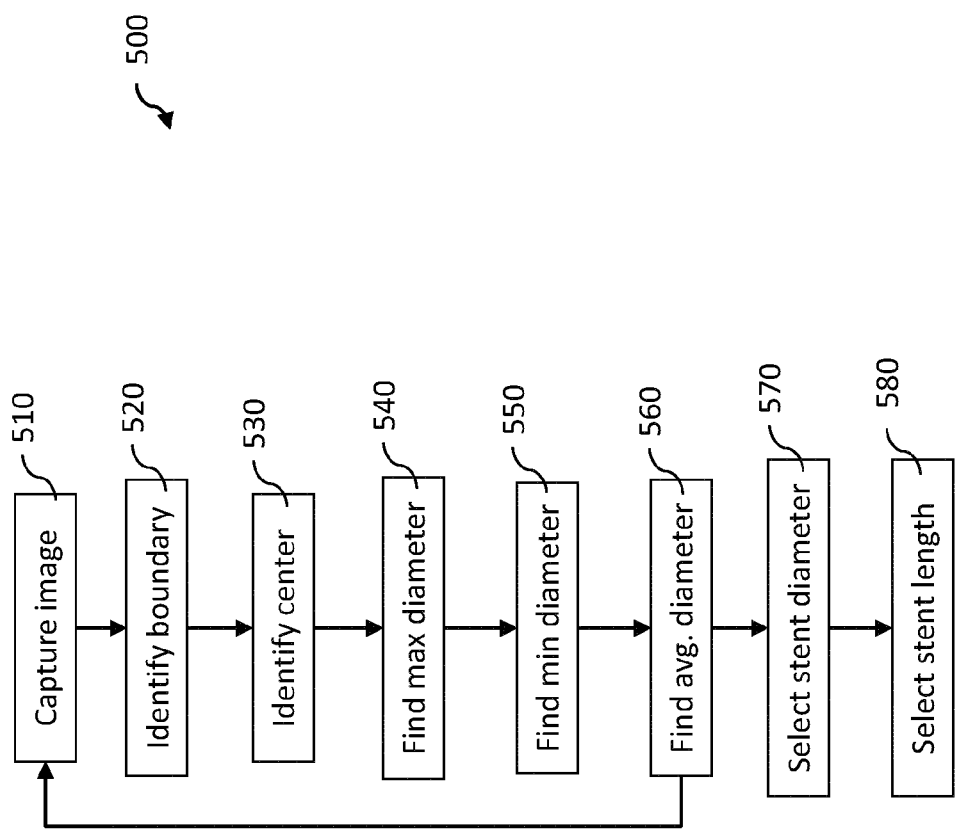
FIG. 5 is a flow diagram for a stent sizing procedure, according to aspects of the present disclosure.

FIG. 5 is a flow diagram 500 for a stent sizing procedure according to the related art. In step 510, an intraluminal image is captured by an intraluminal imaging probe. In step 520, the lumen boundary is identified, either manually by a clinician or automatically by an algorithm. In step 530, the center of the lumen is identified, and in steps 540 and 550 the minimum lumen diameter (e.g., the shortest line connecting any two points of the lumen boundary through the lumen center) and maximum lumen diameter (e.g., the longest line connecting any two points of the lumen boundary through the lumen center) are identified. In step 560, the average lumen diameter is estimated as the average value of the min and max diameters. In step 570, a clinician selects a stent diameter based on the average lumen diameter of the healthy tissue proximal and distal to the vessel's narrowest point. It is common for a clinician to select a stent diameter that adds a "fudge factor" of 1-2 mm to the average lumen diameter. In step 580, the clinician selects a stent length based on a visual perception of the length of the diseased section of the vessel (e.g., a portion of the vessel that includes a stenosis to be propped open with the stent).

This process may be time consuming and of limited accuracy, creating a need in the art for improved tools and procedures.

Figure 6A:
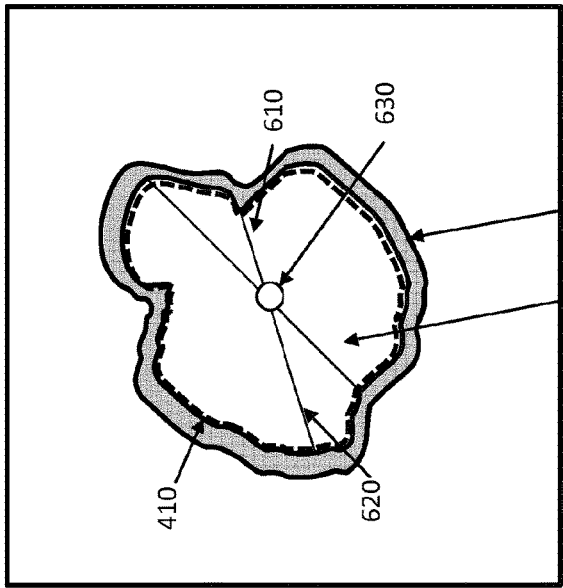
FIG. 6a is a cross-sectional view of a vessel with computed minimum and maximum diameters in which the vessel wall includes a convex, nearly circular geometry, according to aspects of the present disclosure.
Figure 6B:
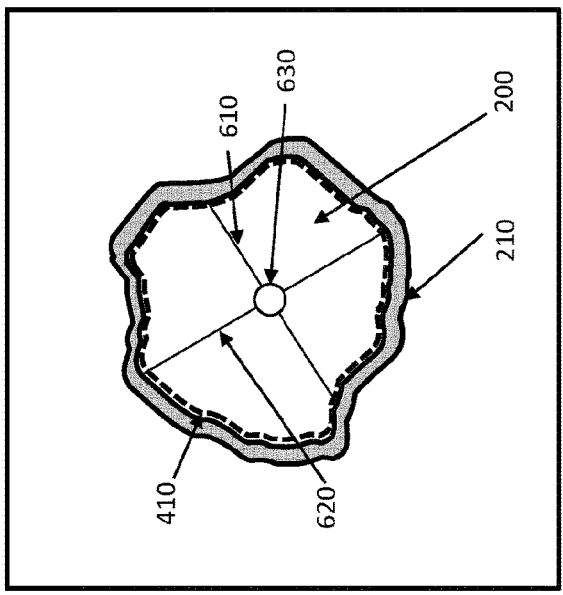
FIG. 6b is a cross-sectional view of a vessel with computed minimum and maximum diameters in which the vessel wall includes a complex, partially concave geometry, according to aspects of the present disclosure.
Figure 6C:
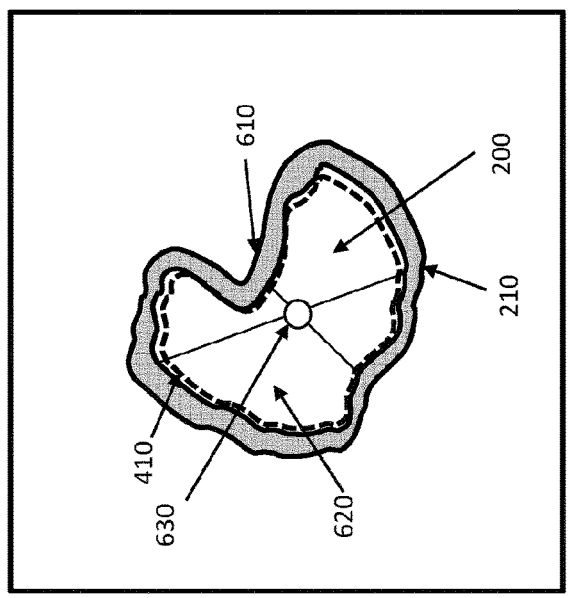
FIG. 6c is a cross-sectional view of a vessel with computed minimum and maximum diameters in which the vessel wall includes a concave cross section, according to aspects of the present disclosure.

FIGS. 6a-6c show the process of finding the minimum and maximum lumen diameter for different vessel cross-sections, according to aspects of the present disclosure.

FIG. 6a shows minimum and maximum diameters for a vessel 200 with a vessel wall 210 that assumes a convex, nearly circular geometry, in accordance with aspects of the present disclosure. The lumen boundary 410 has been identified (e.g., though image recognition). The minimum diameter 610 is the shortest line connecting any two points on the lumen boundary 410 through the lumen center 630. The maximum diameter 620 is the longest line connecting any two points on the lumen boundary 410 through the lumen center 630. In this example, the minimum and maximum diameters have similar values and are separated by a substantial angle. As a result, the average of the minimum and maximum diameters may offer a reasonable approximation of the effective lumen diameter.

FIG. 6b shows minimum and maximum diameters for a vessel 200 with a vessel wall 210 that assumes a complex, partially concave cross-section, in accordance with aspects of the present disclosure. Minimum and maximum diameters are calculated as described above. However, in this example, there is a substantial difference between the minimum and maximum diameters. The lines representing the minimum and maximum diameters are also separated by only a relatively small angle, thus providing little information about what is going on elsewhere around the perimeter of the vessel. In this instance, the average of the minimum and maximum diameters may not be an accurate measure of the effective lumen diameter. Thus, stent sizing based on the average diameter may be inaccurate.

FIG. 6c shows minimum and maximum diameters for a vessel 200 with a vessel wall 210 that assumes a concave (e.g., bean-shaped) cross section, in accordance with aspects of the present disclosure. Minimum and maximum diameters are calculated as described above. However, in this example, there is a large difference (e.g., a factor of two or more) between the minimum and maximum diameters. In this instance, the average of the minimum and maximum diameters will significantly underestimate the actual fluid-carrying capacity of the vessel if propped open to a circular shape, and thus a stent diameter selected based on this value is likely to be smaller than the vessel can actually support.

Referring generally to FIGS. 6a-6c, it will be understood that using the described maximum and minimum diameter approach for determining vessel and/or stent size may not be reliable, in some circumstances. For example, while the maximum and minimum diameter approach to estimating vessel size may offer a reasonable approximation of the lumen diameter (and a corresponding stent diameter) for the vessel in FIG. 6a, that approach may not be as reliable for other vessel shapes, such as those shown in FIGS. 6b and 6c. Accordingly, it may be beneficial to employ an approach to determining vessel size and/or stent size that does not rely on a plurality of maximum and minimum vessel diameters determined with respect to the vessel's center. In that regard, the present disclosure describes methods, and associated systems and devices, for determining vessel size and/or stent size by computing or measuring non-diametric geometries of the vessel (e.g., perimeter, cross-sectional area, volume), and calculating the size of the vessel using an assumption of circularity.

Figure 7A:
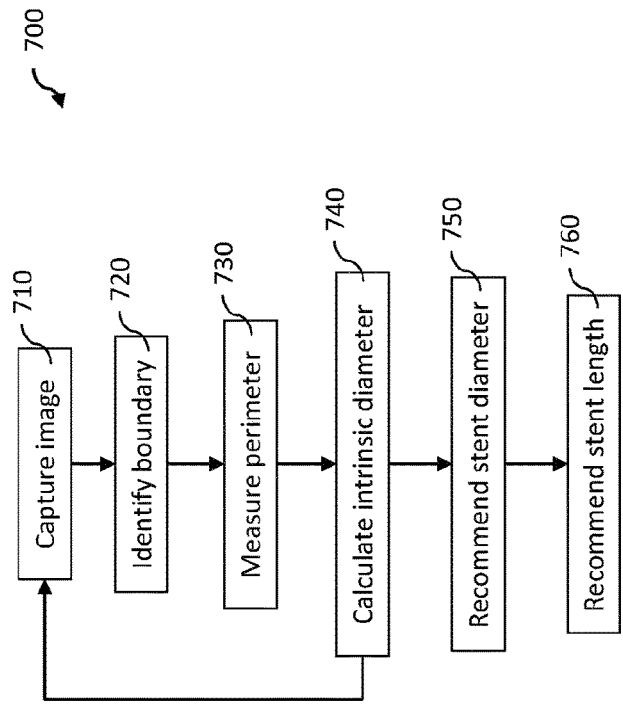
FIG. 7a is a flow diagram for a stent sizing procedure, according to aspects of the present disclosure.

FIG. 7a shows a flow diagram 700 for a stent sizing procedure using a determined vessel perimeter. In step 710, an intraluminal image is captured by an intraluminal imaging catheter or guidewire. The intraluminal image is then transmitted to, and received by, a processor circuit of the intraluminal imaging system. It will be understood that, in some embodiments, a plurality of intraluminal images is captured or obtained by the intraluminal imaging catheter or guidewire, and subsequently received by the processor circuit.

In step 720, the system identifies the lumen boundary or vessel boundary 410 through an image processing and image recognition algorithm. Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety. In some embodiments, manual identification of the lumen boundary may be accomplished at this step (e.g., by a clinician using a touchscreen interface).

In step 730, the system computes a value of the anatomy, such as a geometric value of the anatomy. For example, the system may compute a geometric value associated with any suitable anatomical structure or body lumen including a blood vessel, blood vessel lumen, an esophagus, eustachian tube, urethra, fallopian tube, intestine, colon, and/or any other suitable anatomical structure or body lumen. In the illustrated embodiment, the geometric value comprises the perimeter of the lumen boundary of a blood vessel. This may be done for example by counting pixels and converting to distances at a known ratio (e.g., 0.05 mm per pixel, based on a Field of View (FOV) setting). In some embodiments, the geometric value comprises the outer perimeter of the vessel wall. In some embodiments, the geometric value comprises a perimeter determined or computed at a mid-plaque region of the vessel corresponding to a center of the plaque thickness around the lumen.

In step 740, the system calculates an intrinsic diameter for the anatomy (e.g., lumen or vessel) based on the measured perimeter, which represents the diameter the perimeter would have if it were assumed or estimated to be circular, e.g., expanded to a circular cross section. Accordingly, in some embodiments, calculating the intrinsic diameter for the anatomy includes assuming or estimating the shape of the anatomy to be circular. For example, assuming or estimating the shape of a blood vessel lumen to be circular may involve using the measured or calculated perimeter as though it were the perimeter of a circle. Given the computed length of a vascular perimeter contour (P) and assuming or estimating a circular geometry for the vessel and/or stent, the perimeter-based intrinsic diameter $D_p$ can be derived from the equation:

$$D_p = 2R = P/\pi$$

Once the intrinsic diameter for the current frame is calculated, execution returns to step 710 unless the pullback sequence is complete, in which case execution proceeds to step 750. In some instances, the estimation of circularity involves transforming a non-circular shape into a circular one and then measuring it. This transformation may be mathematical (e.g., a transformation matrix), or may be conceptual, such as assuming or estimating the perimeter of a noncircular shape to be the perimeter of a circular shape. In other instances, the estimate of circularity proceeds as described above, without transformation of the vessel shape. In some instances, the difference between the actual vessel shape and an assumed or estimated circular shape is not significant, as the vessel may already exhibit a substantially circular cross section. In other instances, the difference between the actual vessel shape and an assumed or estimated circular shape is quite significant, as the vessel may exhibit a concave or bean-shaped cross section. Accordingly, an estimation of circularity transforms the actual perimeter of the lumen into a circular shape to varying degrees. In some embodiments, the intrinsic diameter represents the diameter of the lumen of the blood vessel. In some embodiments, the intrinsic diameter represents an inner diameter of the blood vessel, which may be the diameter of defined by the vessel wall. In some embodiments, the intrinsic diameter represents a mid-plaque to mid-plaque diameter of the vessel corresponding to a center of the plaque thickness around the lumen.

In step 750, the system optionally recommends a stent diameter to the clinician or other user that is based on the determined perimeter-based intrinsic diameter. In some embodiments, the recommended stent diameter may be equal to the perimeter-based intrinsic diameter $D_p$ of the healthy tissue of a blood vessel proximal and distal to its narrowest (e.g., smallest perimeter) point. In other instances, the recommended stent diameter may be related to the perimeter-based intrinsic diameter $D_p$ by a fixed ratio or percentage (e.g., 95% or 105% of the perimeter-based intrinsic diameter), and may optionally be modified by the clinician by an additional factor.

It is noted that the assumption of circularity is itself an approximation; an ideally expanded stent may have a circular cross-section, but axial and radial forces acting on the stent may cause slightly asymmetric expansion that causes its cross section to deviate from true circularity. Nevertheless, the assumption of circularity may provide a reliable estimate of the correct stent size.

In step 760, the system recommends a stent length based on the determined perimeter-based intrinsic diameter. This may for example be equal to the number of frames of tissue that show stenosis according to the image recognition algorithms, multiplied by pullback speed and divided by the frame rate, plus a fixed safety margin (e.g., 2 mm).

Figure 7B:
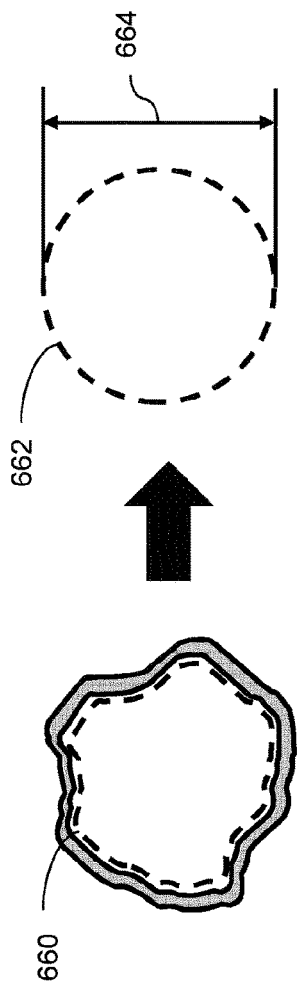
FIG. 7b is a flow diagram illustrating aspects of the stent sizing procedure shown in FIG. 7a, according to aspects of the present disclosure.

FIG. 7b is a diagram illustrating aspects of the method 700. In that regard, FIG. 7b shows an irregular vessel having lumen perimeter 660. The lumen perimeter 660 may be computed using, for example, the boundary detection and quantification techniques referenced above. The lumen perimeter 660 is transformed into, or assumed or estimated to be, a circle 662 of equal perimeter size. Accordingly, assuming a circular shape, a circle 662 of the size of the perimeter 660 is determined to have a diameter 664, which would be the diameter if the irregular vessel assumed a circular shape. Thus, the diameter 664 of the circle 662 may be used as a perimeter-based intrinsic diameter of the vessel lumen.

Figure 8A:
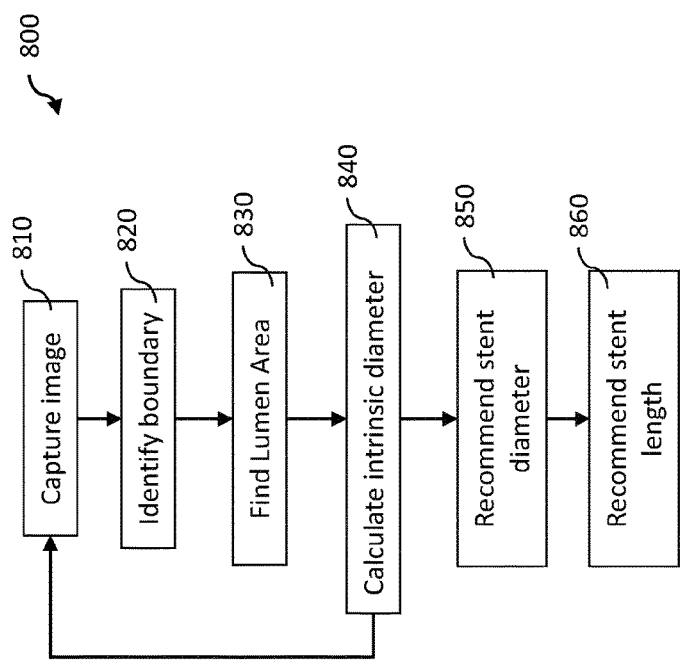
FIG. 8a is a flow diagram for a stent sizing procedure, according to aspects of the present disclosure.

FIG. 8a shows a flow diagram 800 for a stent sizing procedure using a determined lumen area, according to at least one embodiment of the present disclosure, as shown for example in FIG. 6e. In step 810, an intraluminal image is captured by the intraluminal imaging probe 102.

In step 820, the system identifies the lumen boundary or vessel boundary 410 through the image processing and image recognition algorithm.

In step 830, the system computes a geometric value associated with the anatomy (e.g., a vessel or lumen). In the illustrated embodiment, the geometric value comprises the cross-sectional area of the vessel lumen. This may be done for example by counting pixels and converting to distances at a known ratio (e.g., 0.0025 mm² per pixel, based on the Field of View setting). In some embodiments, the geometric value may be a cross-sectional area that includes the vessel wall.

In step 840, the system calculates an area-based intrinsic diameter for the lumen or vessel, which represents the diameter the vessel would have if it were expanded to a circular cross section. Given the area A enclosed by a vascular contour (e.g. the lumen or vessel boundaries of the blood vessel) and estimating a circular geometry for the vessel and/or stent, the area-based intrinsic diameter $D_a$ can be derived from the following equation:

$$D_a = 2R = 2\sqrt{\frac{A}{\pi}}$$

Once the intrinsic diameter for the current frame is calculated, execution returns to step 810 unless the pullback sequence is complete, in which case execution proceeds to step 850.

In step 850, the system determines and recommends a stent diameter to the clinician or other user that is based on the determined area-based intrinsic diameter. In some embodiments, the recommended stent diameter may be equal to the area-based intrinsic diameter $D_a$ of the healthy tissue of the vessel proximal and distal to its narrowest (e.g., smallest cross-sectional area) point. In other instances, the recommended stent diameter may be related to the area-based intrinsic diameter $D_a$ by a fixed ratio or percentage (e.g., 95% or 105% of the Area Intrinsic Diameter).

In step 760, the system recommends a stent length. This may for example be equal to the number of frames of tissue that show stenosis according to the image recognition algorithms, multiplied by pullback speed and divided by the frame rate, plus a fixed safety margin (e.g., 2 mm).

Figure 8B:
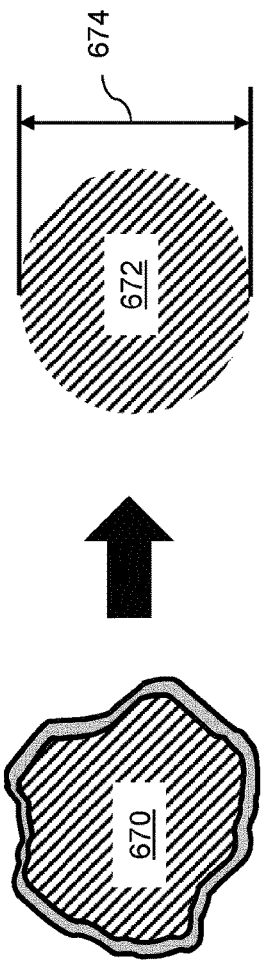
FIG. 8b is a flow diagram illustrating aspects of the stent sizing procedure shown in FIG. 8a, according to aspects of the present disclosure.

FIG. 8b is a diagram illustrating aspects of the method 800. In that regard, FIG. 8b shows an irregular vessel having lumen area 670. The lumen area 670 may be computed using, for example, the boundary detection and quantification techniques referenced above. The lumen area 670 is transformed into, or assumed or estimated to be, a circle having an area 672 equal to the area 670. Accordingly, assuming a circular shape, a circle of the same cross sectional area 672 as the cross sectional area 670 of the irregular lumen is determined to have a diameter 674, which would be the diameter if the irregular vessel assumed a circular shape. Thus, the diameter 674 of the circle may be used as a cross-sectional area-based intrinsic diameter of the vessel lumen.

Figure 9A:
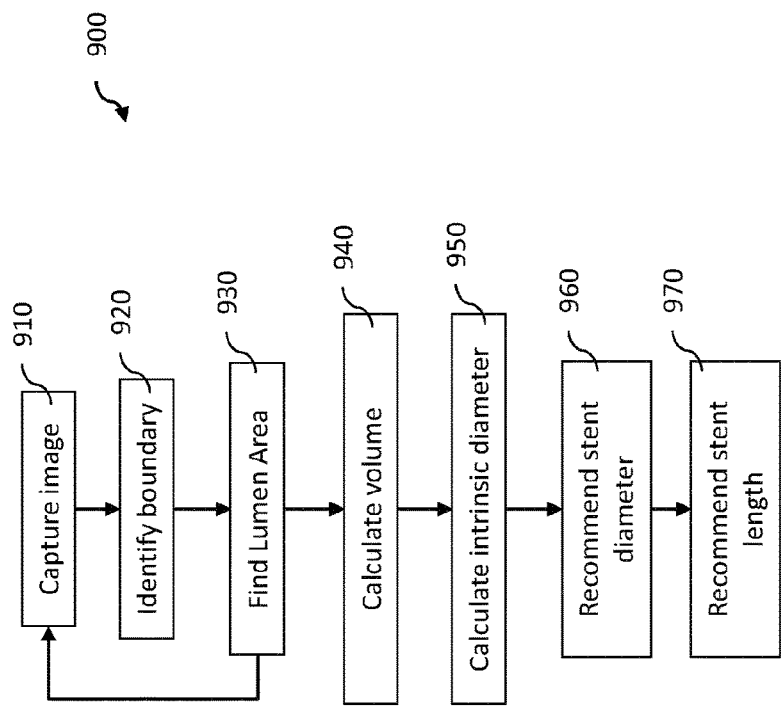
FIG. 9a is a flow diagram for a stent sizing procedure, according to aspects of the present disclosure.

FIG. 9a shows a flow diagram 900 for a stent sizing procedure using a determined vessel volume, according to at least one embodiment of the present disclosure, as shown for example in FIG. 6f. In step 910, an intraluminal image is captured by the intraluminal imaging probe 102.

In step 920, the system identifies the lumen boundary or vessel boundary 410 through the image processing and image recognition algorithm.

In step 930, the system the system computes a geometric value associated with the anatomy (e.g., a vessel or lumen). In the illustrated embodiment, the geometric value comprises the volume of a length of the lumen. This may be performed as part of a pull-back procedure by obtaining a sequence or set of intraluminal images at different longitudinal positions with the lumen, and generating a three-dimensional volumetric image or data set based on the sequence or set of intraluminal images.

In step 940, the system calculates the volume of a region of the vessel (e.g., five or ten consecutive frames) in a healthy area immediately proximal or distal to the region to be stented. This may be done for example by multiplying the known or measured distance between frames by the cross-sectional area of each frame in the region for which a stenosis is detected. In step 950, the system calculates a volume-based intrinsic diameter for the lumen or vessel, which represents the diameter the lumen or vessel would have if it were expanded to a circular cross section. Given the volume V enclosed by a stack vascular contour (e.g. the lumen or vessel boundaries of the blood vessel) and estimating a circular geometry for the vessel and/or stent, the volume-based intrinsic diameter $D_v$ can be derived from the following equation:

$$D_v = 2R = 2\sqrt{\frac{V}{H\pi}}$$

The volume of a stack of vascular contours can be calculated using Simpson's rule. In this instance H is the length of vessel represented by the stack of contours (i.e. the length of vessel covered by the imaging frames from which the vessel contours are obtained). Due to imaging conditions and the difficulty in imaging at an orthogonal cross section, an intrinsic diameter based on volume built from successive imaging cross sections can be more representative of the actual intrinsic diameter measurement that can be related to stent sizing. However, because it requires geometric information from multiple frames at once, the $D_v$ calculation may not be performed on a per-frame basis, whereas $D_p$ and $D_a$ may be calculated separately for each frame.

Calculation of the intrinsic vessel diameter relies on the tendency or ability of vessels to assume a circular shape. The circular shape assumption also applies to stents, which may be generally circular and sized based on their diameter and length. The volume-based intrinsic diameter may be particularly relevant to scenarios in which the vessel is deformed and its contours are not circular or convex. In such scenarios, the contour perimeter, the area enclosed by a contour, and/or the volume enclosed by a stack of contours may still be generated. Using any of those measurements the intrinsic diameter of the vessel may be derived by using the algorithms and relationships shown above.

In step 960, the system recommends a stent diameter to the clinician or other user that is based on the volume-based intrinsic diameter. In some embodiments, the recommended stent diameter may be equal to the volume-based intrinsic diameter $D_v$. In other instances, the recommended stent diameter may be related to the volume-based intrinsic diameter $D_v$ by a fixed ratio or percentage (e.g., 95% or 105% of the Volume Intrinsic Diameter).

In step 970, the system recommends a stent length. This may for example be equal to the number of frames of tissue that show stenosis according to the image recognition algorithms, multiplied by pullback speed and divided by the frame rate, plus a fixed safety margin (e.g., 2 mm).

In some embodiments, the desired stent length may be calculated based on automatic measurements from co-registered external images (e.g., fluoroscopic images) in addition to or instead of automatic measurements based on the plurality of intravascular images. In some embodiments, frame-to-frame local differences in diameter, area, or volume measurements of the vessel or lumen may be smoothed or averaged to provide averaged measurements.

Figure 9B:
FIG. 9b is a flow diagram illustrating aspects of the stent sizing procedure shown in FIG. 9a, according to aspects of the present disclosure.

FIG. 9b is a diagram illustrating aspects of the method 900. In that regard, FIG. 9b shows an irregular vessel having lumen volume 680. The lumen volume 680 may be computed using, for example, the boundary detection and quantification techniques referenced above with respect to a plurality of cross-sectional images obtained at different longitudinal positions within the vessel. The lumen volume 680 is transformed into a cylinder having an volume 682 equal to the volume 680. Accordingly, estimating a cylindrical shape, a cylinder of the same length and volume 682 as the length and volume 680 of the irregular lumen is determined to have a diameter 684, which would be the diameter if the irregular vessel assumed a cylindrical shape. Thus, the diameter 684 of the cylinder may be used as a cross-sectional volume-based intrinsic diameter of the vessel lumen.

Figure 10:
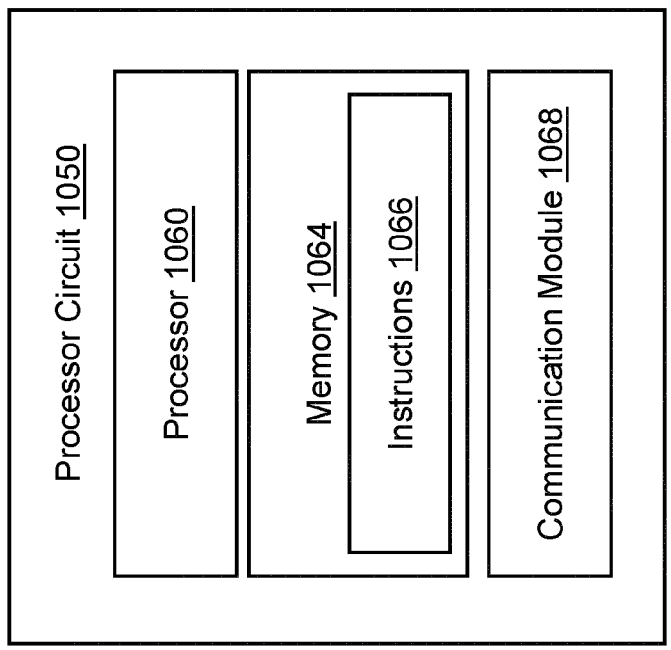
FIG. 10 is a schematic diagram of a processor circuit, according to aspects of the present disclosure.

FIG. 10 is a schematic diagram of a processor circuit 1050, according to embodiments of the present disclosure. The processor circuit 1050 may be implemented in the ultrasound imaging system 100, or other devices or workstations (e.g., third-party workstations, network routers, etc.) as necessary to implement one or more of the methods disclosed herein, including the methods 500, 700, 800, and/or 900. As shown, the processor circuit 1050 may include a processor 1060, a memory 1064, and a communication module 1068. These elements may be in direct or indirect communication with each other, for example via one or more buses.

The processor 1060 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1060 may also comprise another hardware device, a firmware device, or any combination thereof configured to perform the operations described herein. The processor 1060 may also be implemented as a combination of computing devices, e.g., a combination of a DSP and a microprocessor, a plurality of microprocessors, one or more microprocessors in conjunction with a DSP core, or any other such configuration.

The memory 1064 may include a cache memory (e.g., a cache memory of the processor 1060), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1064 includes a non-transitory computer-readable medium. The memory 1064 may store instructions 1066. The instructions 1066 may include instructions that, when executed by the processor 1060, cause the processor 1060 to perform the operations described herein, including one or more steps of the methods 500, 700, 800, and/or 900. Instructions 1066 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 1068 can include any electronic circuitry and/or logic circuitry to facilitate direct or indirect communication of data between the processor circuit 1050, and other processors or devices. In that regard, communication module 1068 can be an input/output (I/O) device. In some instances, the communication module 1068 facilitates direct or indirect communication between various elements of the processor circuit 1050 and/or the ultrasound imaging system 100. The communication module 1068 may communicate within the processor circuit 1050 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the lumen intrinsic diameter measurement system may be employed in anatomical systems within the body other than those described, or may be employed to image other disease types, object types, or procedure types than those described. The technology described herein may be applied to intraluminal imaging sensors of diverse types, whether currently in existence or hereinafter developed. The system may be employed with IVUS for coronary arterial and peripheral use in arterial or venous imaging, such as PHILIPS' IGT-D devices and IVUS console software. In some embodiments, the intrinsic diameter may be calculated by several different methods, and the most appropriate (e.g., most conservative) value selected. In other embodiments, the user may select which method to use in calculating vessel diameter.

Accordingly, the logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the lumen intrinsic diameter measurement system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or."

Unless otherwise noted in the claims, stated values shall be interpreted as illustrative only and shall not be taken to be limiting.

The above specification, examples and data provide a complete description of the structure and use of exemplary embodiments of the lumen intrinsic diameter measurement system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intravascular imaging system comprising:
    an intravascular imaging catheter or guidewire configured to be positioned within a blood vessel of a patient;
    a processor circuit in communication with the intravascular imaging catheter or guidewire, wherein the processor circuit is configured to:
    receive a plurality of cross-sectional images of the blood vessel from the intravascular imaging catheter or guidewire;
    perform an anatomical measurement of the blood vessel using image processing of at least one cross-sectional image of the plurality of cross-sectional images;
    generate an idealized shape comprising:
    a circular cross-section; and
    a size comprising a value of the anatomical measurement;
    calculate a diameter of the idealized shape;
    calculate a stent diameter that is equal to the diameter of the idealized shape multiplied by a scaling factor; and
    output the stent diameter to a display in communication with the processor circuit.

2. The intravascular imaging system of claim 1, wherein the anatomical measurement comprises a perimeter of the blood vessel.

3. The intravascular imaging system of claim 1, wherein the anatomical measurement comprises a cross-sectional area of the blood vessel.

4. The intravascular imaging system of claim 1, wherein the anatomical measurement comprises a volume of the blood vessel.

5. The intravascular imaging system of claim 1, wherein the anatomical measurement comprises at least two of a perimeter, a cross-sectional area, or a volume of the blood vessel.

6. The intravascular imaging system of claim 1, wherein the processor circuit is further configured to output the diameter of the idealized shape to the display.

7. The intravascular imaging system of claim 1,
    further comprising a user interface in communication with the processor circuit, wherein the user interface is configured to accept a user input, and wherein the processor circuit is configured to perform the calculation of the stent diameter and the output of the stent diameter in response to receiving the user input from the user interface.

8. The intravascular imaging system of claim 1, wherein the processor circuit is further configured to:

calculate a stent length based on the plurality of cross-sectional images; and output the stent length to the display.

9. A method, comprising:

receiving, by a processor circuit, a plurality of cross-sectional images of a blood vessel of a patient, wherein the plurality of cross-sectional images is obtained by an intravascular imaging catheter or guidewire positioned within the blood vessel;

performing an anatomical measurement of the blood vessel using image processing by the processor circuit of at least one cross-sectional image of the plurality of cross-sectional images;

generating an idealized shape comprising:

a circular cross-sectional shape; and a size comprising a value of the anatomical measurement;

calculating a diameter of the idealized shape;

calculating a stent diameter that is equal to the diameter of the idealized shape multiplied by a scaling factor; and outputting the stent diameter to a display in communication with the processor circuit.

10. The method of claim 9, wherein the anatomical measurement comprises a perimeter of the blood vessel.

11. The method of claim 9, wherein the anatomical measurement comprises cross-sectional area of the blood vessel.

12. The method of claim 9, wherein the anatomical measurement comprises a volume of the blood vessel.

13. The method of claim 9, wherein the anatomical measurement comprises at least two of a perimeter, a cross-sectional area, or a volume of the blood vessel.

14. The method of claim 9, further comprising outputting the diameter of the idealized shape to the display.

15. The method of claim 9, further comprising receiving a user input from a user interface, wherein the calculating the stent diameter and the outputting the stent diameter are performed in response to receive the user input.

16. The method of claim 9, further comprising:

calculating a stent length based on the plurality of cross-sectional images; and outputting the stent length to the display.

17. The intravascular imaging system of claim 1, wherein the anatomical measurement is not a diameter of the blood vessel.

18. The intravascular imaging system of claim 1, wherein the blood vessel is concave-shaped or bean-shaped such that:

a diameter of the blood vessel is not directly measured; and the diameter of the idealized shape comprises an estimate of the diameter of the blood vessel.

* * * * *